US00PP13733P29

(12) United States Plant Patent
Kordes

(10) Patent No.: US PP13,733 P2
(45) Date of Patent: Apr. 22, 2003

(54) MINIATURE ROSE PLANT NAMED 'KORBEFOSA'

(75) Inventor: Tim-Hermann Kordes, Offenseth-Sparrieshoop (DE)

(73) Assignee: W. Kordes Sohne Rosenschulen GmbH & Co., KG (DE)

( * ) Notice: Subject to any disclaimer, the term of this patent is extended or adjusted under 35 U.S.C. 154(b) by 0 days.

(21) Appl. No.: 09/993,225

(22) Filed: Nov. 6, 2001

(51) Int. Cl.[7] ..... A01H 5/00

(52) U.S. Cl. ..... Plt./121

(58) Field of Search ..... Plt./121

*Primary Examiner*—Bruce R. Campell
*Assistant Examiner*—W C Haas
(74) *Attorney, Agent, or Firm*—Webb Ziesenhiem Logsdon Orkin & Hanson, P.C.

(57) ABSTRACT

A new miniature rose plant which has abundant, light pink colored flowers and attractive foliage. The variety successfully propagates from softwood cuttings and is suitable for year round production in commercial glasshouses as a flowering pot plant.

2 Drawing Sheets

BOTANICAL CLASSIFICATION

*Rosa hybrida.*

BACKGROUND OF THE NEW PLANT

The present invention constitutes a new and distinct variety of miniature rose plant named 'KORbefosa' which was developed by artificially pollinating an unnamed seedling (unpatented) with an unnamed seedling (unpatented).

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'KORbefosa' from other varieties.

The two parents were crossed in the summer of 1999 and the resulting seed was sown in December 1999 in a controlled greenhouse environment. The seeds from hybridization were planted in a controlled environment in Klein Offenseth, Sparrieshoop, Germany and evaluations were conducted on the resulting plants.

SUMMARY OF THE INVENTION

Asexual reproduction of 'KORbefosa' by softwood cuttings was first done in Denmark and later in California in controlled greenhouse environments. The characteristics of the new variety remain as true to type through successive propagations.

The new variety may be distinguished from its seed parent, an unnamed breeding seedling, by the following combination of characteristics:

1. 'KORbefosa' has medium double flowers, while the seed parent has big single flowers.

2. 'KORbefosa' has light pink colored petals, while the seed parent has dark pink petals.

The new variety may be distinguished from its pollen parent, an unnamed breeding seedling by the following combination of characteristics:

1. 'KORbefosa' has smaller flowers and foliage as compared to the pollen parent.
2. 'KORbefosa' has light pink colored petals, while the pollen parent has dark red petals.

The new variety differs from 'KORmisso', U.S. Plant Pat. No. 11,264 as set forth in Table 1:

TABLE 1

| | 'KORbefosa' | 'KORmisso' |
|---|---|---|
| Petal color, upper surface | Red-Purple Group 63D | Red Group 54B |
| Petal color, reverse surface | Red-Purple Group 63C | Red Group 54B |
| Petal count | 40–45 petals | 50–60 petals |

DESCRIPTION OF THE DRAWINGS

The accompanying color illustrations show as true as is reasonably to obtain in color photographs of this type, the typical characteristics of the buds, flowers, leaves, stems of 'KORbefosa'.

In photo sheet #1.

Figures 1, 2, 3, 4, 5, 6, 7, 8, 9:
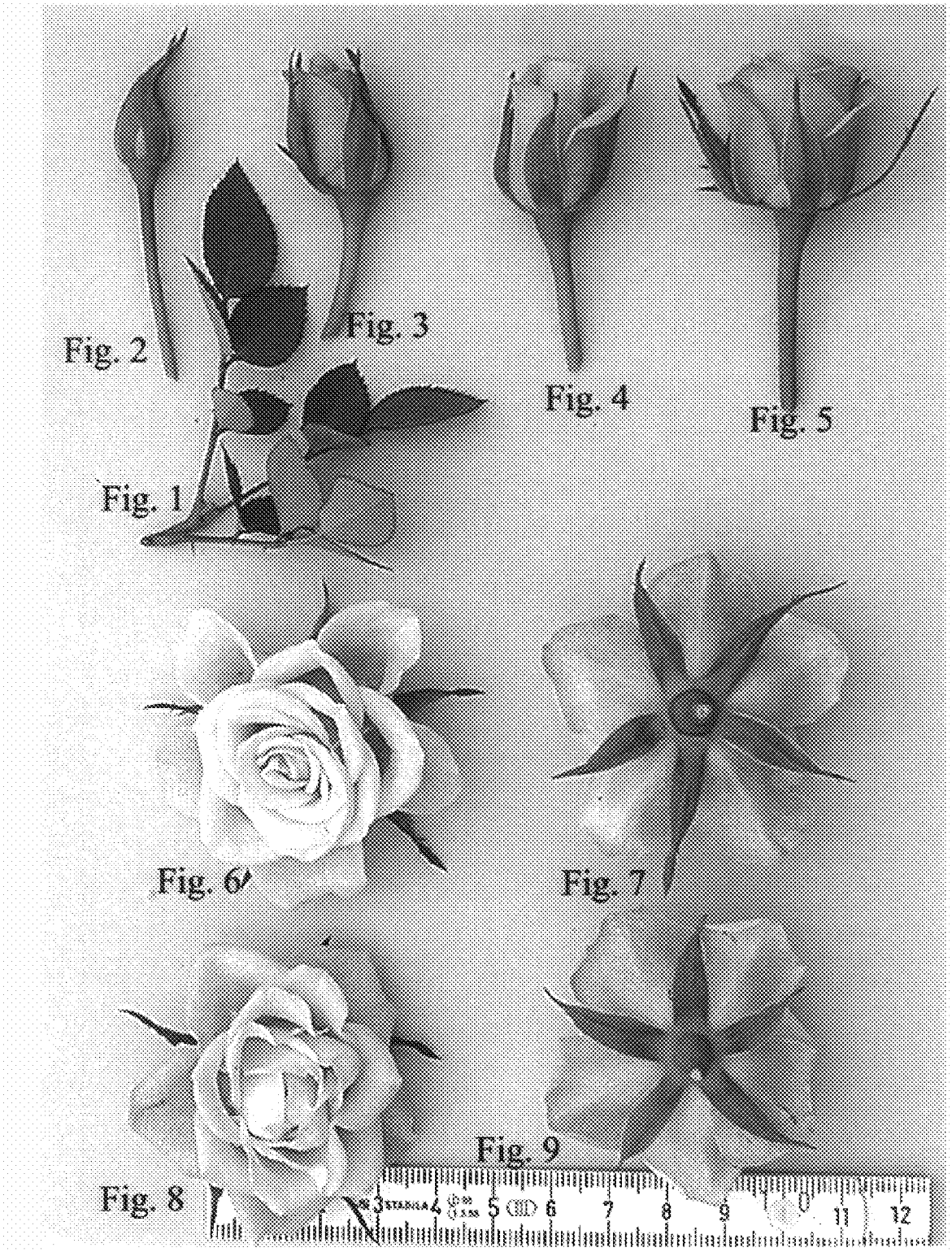
FIG. 1 shows a young shoot.
FIG. 2 shows a bud before opening of the sepals.
FIG. 3 shows a bud at the opening of the sepals.
FIG. 4 shows a bud at the opening of the petals.
FIG. 5 shows a flower during the course of opening.
FIG. 6 shows an open flower, obverse plan view.
FIG. 7 shows an open flower, reverse plan view.
FIG. 8 shows a fully open flower, obverse plan view.
FIG. 9 shows a fully open flower, reverse plan view.
Figures 10, 11, 12, 13, 14, 15, 16, 17, 18:
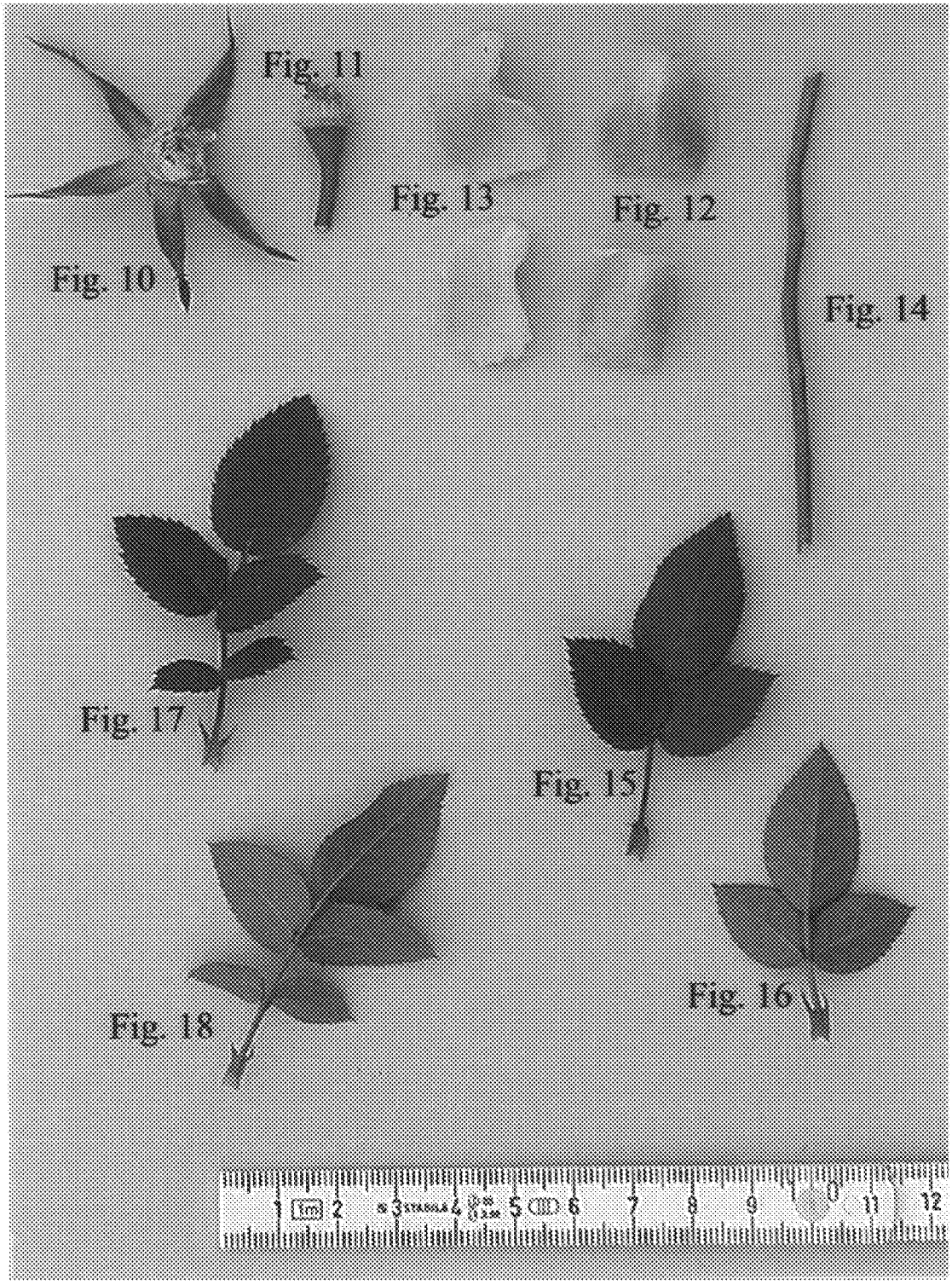

In photo sheet #2:

FIG. 10 shows a receptacle with stamens and pistils.

FIG. 11 shows a receptacle with pistils and stamens removed.

FIG. 12 shows detached flower petals, outer surface.

FIG. 13 shows detached flower petals, inner surface.

FIG. 14 shows a bare stem exhibiting thorns and flower attachment.

FIG. 15 shows three leaflets, upper side.

FIG. 16 shows three leaflets, under side.

FIG. 17 shows five leaflets, upper side.

FIG. 18 shows five leaflets, under side.

DESCRIPTION OF THE NEW PLANT

The following is a detailed description of 'KORbefosa', as observed in its growth in greenhouses in Fraugde, Denmark, and greenhouses in Santa Barbara, Calif., both at 20–25° C. Descriptions were made from plants 11 to 13 weeks old after propagation as produced in a pot treated with growth regulators normally used in the greenhouse production process. The growth regulator Paclobutrazol was applied at 15–30 ppm weekly beginning at a plant age of 8 weeks. The peduncle lengths mentioned may actually be shorter and the foliage color several shades darker than on untreated specimens. Color references are made using The Royal Horticultural Society (London, England) Colour Chart, 1995, except where common terms of color are used.

THE PLANT

Classification:
- *Botanical.*—*Rosa hybrida.*
- *Commercial.*—Miniature.

Plant growth: Moderately vigorous. Grows compact upright to bushy. When grown as a 10 cm pot plant, the average height of the plant itself is 18–20 cm, and average width is 20 cm. When grown as a 15 cm pot plant, the average height of the plant itself is 22–27 cm, and average width is 30 cm. Production time is generally 11 to 13 weeks depending on average temperature, light level, and culture practices.

Stem:
- *Color.*—Young wood: Green Group 138B, with intonations of Red-Purple Group 59C. Older wood: Green Group 138A.
- *Surface.*—Smooth for both young wood and older wood.
- *Diameter.*—2–3 mm.
- *Internode length.*—20–25 mm.
- *Number of internodes.*—5–6.

Thorns:
- *Incidence.*—Few number of thorns.
- *Size.*—2–3 mm.
- *Color.*—Red-Purple Group 59C.
- *Shape.*—Hooked downwards.

FOLIAGE

Arrangement: Alternate, compound with 3–7 leaflets per leaf, generally symmetrical, abundant, and flat in aspect. Stipules at petiole base.

Quantity of leaves: 5–6 per lateral branch.

Leaf size:
- *Length.*—65–70 mm.
- *Width.*—40–45 mm.

Petioles:
- *Color.*—Green Group 138A.
- *Margin.*—Stipitate glands present.
- *Length.*—8–10 mm.
- *Diameter.*—About 1 mm.

Stipules:
- *Size.*—4–5 mm.
- *Surface.*—Smooth.
- *Color.*—Green Group 138D, with intonations of Red-Purple Group 59B.
- *Margin.*—Stipitate glands present.

Rachis:
- *Color.*—Green Group 138B, with intonations of Red-Purple Group 59B.
- *Margin.*—Stipitate glands present.
- *Length.*—10–25 mm.

Leaflets:
- *Margin.*—Serrated.
- *Shape.*—Ovate with acute apex and obtuse base.
- *Texture.*—Smooth.
- *Appearance.*—Dull.
- *Size.*—Length: 15–30 mm. Width: 5–20 mm.
- *Color.*—Young foliage: Upper surface: Green Group 138A. Lower surface: Greyed-Green Group 191C, with intonations of Red-Purple Group 59B. Mature foliage: Upper surface: Green Group 137B. Lower surface: Greyed-Green Group 189B.

INFLORESCENCE

Blooming habit: Recurrent.

Number of flowers: Generally 1 bud per flowering stem.

Peduncle:
- *Color.*—Green Group 146C, with intonations of Red-Purple Group 59B.
- *Texture.*—Smooth, with pubescence.
- *Length.*—30–35 mm.
- *Form.*—Upright.

Receptacle:
- *Surface.*—Smooth, glabrous.
- *Shape.*—Funnel-shaped.
- *Size.*—Height: 5–6 mm. Width: 4–5 mm.
- *Color.*—Green Group 146D.

Sepals:
- *Quantity.*—5.
- *Shape.*—Narrowly ovate with acute tip.
- *Texture.*—Leathery.
- *Margin.*—Foliaceous appendages on three of the five sepals.
- *Appearance.*—Dull.
- *Color.*—Upper surface: Green Group 138B. Reverse surface: Green Group 138B.

Buds:
- *Size when just opening.*—Length: 15–20 mm. Width: 10–12 mm.
- *Shape.*—Pointed.
- *Color.*—Red-Purple Group 62B when just opening.

Flower:
- *Duration.*—As a pot plant, flowers last 16–21 days.
- *Fagrance.*—None.
- *Size.*—55–60 mm in diameter.
- *Form* (*shape when viewed from the side*.—Upon opening: Cupped. Open flower: Cupped.
- *Color.*—Petals, upon opening: Upper surface: Red-Purple Group 63D. Reverse surface: Red-Purple Group 63C. Petals, after opening: Upper surface: Yellow-Green Group 150D shading to Red-Purple Group 65D. Reverse surface: Yellow-Green Group 150D shading to Red-Purple Group 65C.

*Basal petal spots.*—Size: 4–6 mm. Color: Yellow Group 9B.

*General tonality of open flower.*—Yellow Group 6B on third day fading to Yellow Group 4D.

Petals:

*Petal reflex.*—Outermost petals reflex backward at opening; when fully open, all petals reflex backwards.

*Texture.*—Smooth.

*Petal edge.*—Uniform.

*Petal count.*—Approximately 40–45 per flower.

*Petal size.*—Length: 20 mm. Width: 30 mm.

*Shape.*—Outer petals: Ovate. Inner petals: Ovate.

*Petaloids.*—Usually none.

Reproductive organs:

*Stamens.*—Number: Approximately 50–55 per flower. Pollen: Yellow-Orange Group 17A; average amount. Anthers: Size: 1–2 mm. Color: Yellow-Orange Group 17A. Shape: Oblong. Filaments: Size: 2–3 mm. Color: Yellow-Orange Group 17A.

*Pistils.*—Number: Approximately 60–70 per flower. Stigmas: Location: Below anthers. Color: Yellow Group 1C. Styles: Color: Red Group 43C. Length: 3–4 mm.

GROWTH

Vegetation: Dense.

Blooming: Abundant.

Aptitude to bear fruit: Poor.

Resistance to diseases: Above average resistance to mildew and Botrytis under normal growing conditions in Fraugde, Denmark and Santa Barbara, Calif.

Hips/seeds: Unknown, the plant has never been grown to the stage of seed development due to the fact that the variety is developed for use as a flowering potted plant only. Winter hardiness and drought/heat tolerance: This variety is a potted flowering plant developed for one time use only and has not been tested for winter hardiness or drought/heat tolerance.

I claim:

1. A new and distinct variety of rose plant substantially as shown and described.

* * * * *